(12) United States Patent  
Nablo et al.

(10) Patent No.: US 7,145,155 B2  
(45) Date of Patent: Dec. 5, 2006

(54) PROCESS FOR ELECTRON STERILIZATION OF A CONTAINER

(75) Inventors: Samuel V. Nablo, Acton, MA (US); Denise A. Cleghorn, Dracut, MA (US); James C. Wood, Jr., Lexington, MA (US)

(73) Assignee: Electron Porcessing Systems, Inc., North Billerica, MA (US)

( * ) Notice: Subject to any disclaimer, the term of this patent is extended or adjusted under 35 U.S.C. 154(b) by 91 days.

(21) Appl. No.: 10/523,668

(22) PCT Filed: Mar. 5, 2003

(86) PCT No.: PCT/US03/06732

§ 371 (c)(1), (2), (4) Date: Apr. 29, 2005

(87) PCT Pub. No.: WO2004/013889

PCT Pub. Date: Feb. 12, 2004

(65) Prior Publication Data

US 2006/0192140 A1    Aug. 31, 2006

Related U.S. Application Data

(60) Provisional application No. 60/401,122, filed on Aug. 5, 2002.

(51) Int. Cl.  
*G21H 5/00* (2006.01)  
*H01J 37/30* (2006.01)

(52) U.S. Cl. ............... 250/492.1; 250/492.3; 250/505.1

(58) Field of Classification Search ............ None  
See application file for complete search history.

(56) References Cited

U.S. PATENT DOCUMENTS 4,983,849 A * 1/1991 Thompson et al. ...... 250/492.3  
7,067,827 B1 * 6/2006 Bol et al. ............... 250/492.2

FOREIGN PATENT DOCUMENTS

JP        11-248897        9/1999

OTHER PUBLICATIONS

Copy of the International Search Report dated Sep. 4, 2003.

* cited by examiner

*Primary Examiner*—Nikita Wells  
(74) *Attorney, Agent, or Firm*—Nields & Lemack

(57) ABSTRACT

Minimum electron energy is used for the sterilization of preformed containers in order to minimize the machinery size, cost and radiation shielding required for in-line use. The electron energy required is reduced by the use of one-sided (unilateral) irradiation wherein the dose delivered by the primary radiation to thicker portions of the containers is supplemented by the dose delivered by scattered electrons.

3 Claims, 10 Drawing Sheets

Unilateral Sterilization Geometry for Fluid Containers

Unilateral Sterilization Geometry for Fluid Containers

VACUUM BOTTLE/JUG GRIPPER—ENDS FREE
ELEVATION AND PLAN VIEWS

SPRING LOADED GRIPPER—ENDS FREE
ELEVATION AND PLAN VIEWS

PROCESS FOR ELECTRON STERILIZATION OF A CONTAINER

This application claims the benefit of provisional application Ser. No. 60/401,122, filed Aug. 5, 2002.

BACKGROUND OF THE INVENTION

1. Field of the Invention

The invention relates to electron processing, and in particular to the sterilization of containers by energetic electrons.

2. Description of the Related Art

The application of energetic electrons to the sterilization of food/pharmaceutical containers has attracted considerable effort in the past[1], much of which has focused on treatment of the food contact surfaces in form-fill-seal[2] or the treatment of preformed containers tumble packed and bagged[3]. Techniques have been published[4, 5] on the in-line electron treatment of containers, typically blown polymers, for application to high speed filling lines. One of the major problems facing the adaptation of such a process to pre-sterilized (aseptic or esl, extended shelf life) filling machinery is the requirement of providing a completely sterile container to the filling equipment. Two major problems exist in this application:

1. The need to support the container in order to control its transport through the sterilizer and
2. The need to control its position and vertical orientation into the filling machine, usually of rotary design.

If inadequate electron energies are used for full penetration of the container walls as in the low energy processes taught earlier[2], then special precautions are necessary in the filler in order to prevent any contamination of the contents by microorganism convective transport to the fill spout/container mouth area or transfer contamination of the pre-sterilized filler region itself by surface borne microorganisms.

Pneumatic transport techniques have been developed[6] and are widely used on such equipment by which the container is moved along horizontally on rails located in grooves blown or molded into the container for this purpose, usually under the container's neck. The fact that these rails must remain in contact with bottles moving at up to 1 m.sec$^{-1}$ in a high speed filler, means that no time is available for bottle rotation or exposure of the rail contact areas and, of course, these sections exposed to the electron beam must be water cooled for dissipation of the electron energy absorbed in the rails.

If a more traditional conveyor is employed, using vacuum hold-down of the erect bottles, for example, then the interface between the bottle bottom and the conveyor plate is inaccessible to the sterilizing flux of energetic electrons. Hence its transport from the in-line sterilizer to the filler can lead to fill-zone contamination. Techniques are available for HEPA or sterile air isolation of the fill-spout/container neck area, but the possibility still exists for the transport of viable microorganisms remaining on the container bottom to the critical, pre-sterilized regions of the filler.

This application teaches techniques, verified experimentally with electron dosimetry, which permit complete sterilization of blow-molded bottles and other open-mouthed containers. It employs container presentation techniques which allow electron access to all surfaces of the container and which do not require rigid gripping or the use of devices which block electron access to those contacted surface areas of the container during the sterilization process.

Current practice for bottle sterilization/disinfection utilizes liquid disinfectants such as paracetic acid and/or hydrogen peroxide, or they may be applied in a spray form. For liquid treatment this requires an extended holding time (8–10 s) of the solution in the container in order to be efficacious, followed by washing and drying to remove residual contaminants on the food contact surfaces. This sequence required large accumulation areas at the filling speeds of interest (e.g. 10 sec$^{-1}$ at 16 oz) and special environmental considerations for handling of the wastewater. Present systems utilize large star wheels, typically with neck grippers, for transport of the containers in a vertical orientation through the above steps and into the pre-sterilized filler region of the system.

SUMMARY OF THE INVENTION

This invention comprehends a process for electron sterilization of all surfaces of open-mouthed containers, cups or bottles, where the sterilizing energy is directed laterally at the sidewall of the container in a sheet extending beyond the ends of the container, so that the dose delivered by the primary radiation to both the exterior and interior surfaces of the container is supplemented by scattered radiation.

BRIEF DESCRIPTION OF THE DRAWINGS

This invention may best be understood from the following detailed description thereof, having reference to the accompanying drawings, in which:

FIG. 7 (FIGS. 7a and 7b) is a diagram showing bottom exterior and interior regions of 3-quart jug treated as in FIG. 3; FIG. 7b is a diagrammatic rearrangement of the dose data of FIG. 7a;

DESCRIPTION OF THE PREFERRED EMBODIMENTS

Purpose of the Process

Figure 1:
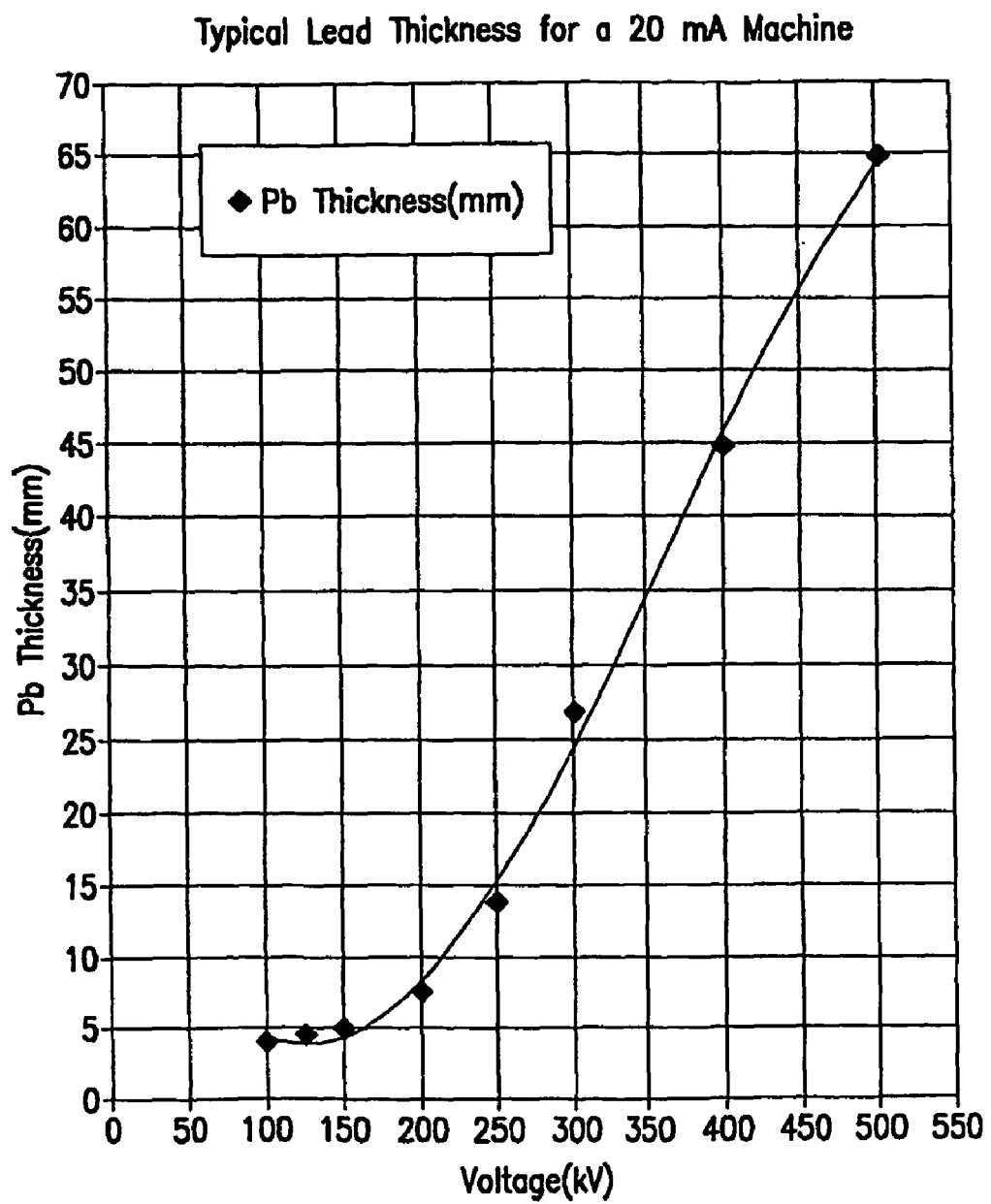
FIG. 1 is a graph showing typical lead thickness as a function of operating voltage for a 20 mA machine.

The teaching of this application is directed to the use of minimum electron energy for the sterilization of preformed containers in order to minimize the machinery size, cost and radiation shielding required for in-line use. These sterilizers are designed to permit use in uncontrolled areas which means that the X-ray levels at the surfaces for the system must be reduced to levels acceptable for continuous human occupancy, typically 0.05 millirem/h or 0.5μ Gy/h[7]. An indication of the lead thicknesses required to reduce a sterilizer of modest power to these levels is shown[8] in FIG. 1. The goal of the system designer then is to arrive at an operating voltage for the accelerator which provides electrons of adequate energy to sterilize all surfaces of the container while subjecting those regions which are easily treated, such as the container's outer surface, to dose levels which are acceptable. That is, a dose uniformity is sought which provides an acceptable maximum dose when the minimum treatment level is that required by the filling/capping process. Other work[9] with *B. pumilus* (ATCC 27142) has shown this to be 10 kGy for the 6 Log Count Reduction (LCR) required for aseptic filling. Such a dose requires the deposition of 2.4 calories/g to the container surfaces. High non-uniformity, say ten or twenty to one, might therefore lead to energy deposition levels capable of thermal deformation of polymer containers, or excessive color center formation in glass. Such excess levels are encountered in processes such as described in U.S. Pat. No. 3,780,308 or in U.S. Pat. No. 6,221,216 where large volume containers must be treated through small area openings (that is, the fill mouth). A novel approach involving isotropic irradiation of a container for low speed (6 min$^{-1}$) container sterilization has been described by Sadat and Huber[10] but such an approach is impractical for high speed (100–1000 min$^{-1}$) filling applications addressed here. More complex bilateral irradiation techniques have been described for the sterilization of tubular containers[4] but have not been commercialized.

Requirement of the Process

The need to achieve a minimum surface treatment[9] with one-sided (unilateral) irradiation is challenged by the thicknesses for the container walls (in particular the thick bottom of blow molded polymer bottles or jugs) and the heavy walls of structurally strengthened regions of the container—such as the neck and, if screw capped, threaded regions. Because the main interest in the application of this art is in the filling of 250 ml to 4 liter containers for liquid foodstuffs, a typical 1 liter polyester bottle will be used to illustrate the unexpected features of the process. The wall thicknesses over the 3-cm long neck region of such a container will range from 0.16 to 0.23 cm in thickness or, for polyester, for example, with a density of 1.2 g.cm$^{-3}$, a weight per unit area of 1900–2800 g.m$^{-2}$. Areas in the bottom of blow molded polymer containers can range above these figures, to 3600 g.m$^{-2}$ or more.

Figure 2:
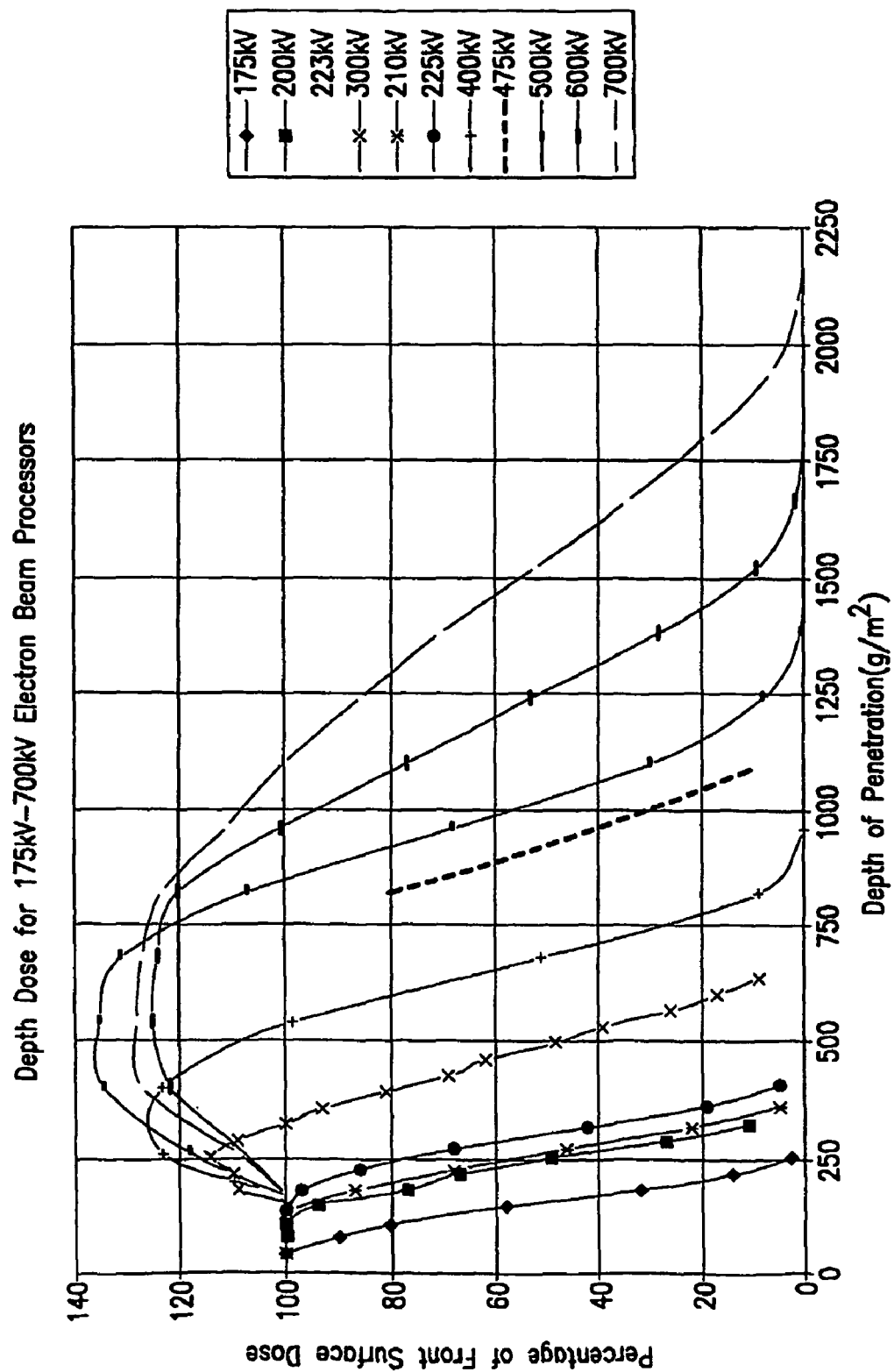
FIG. 2 is a graph showing depth dose for 175 kV–700 kV electron beam processors.

The penetration of electrons in matter varies with this measure of areal density since the deposition of energy by the primary electron is determined by multiple electron-electron collisions. The electron density in matter is measured by this areal density figure, so that penetration depths are given (and displayed) in these units. FIG. 2 shows some measured[12] penetration curves for electron sterilizers (accelerators) working at various energies. One can see that very high voltages (energies) are involved in the penetration of matter above 1000 g.m$^{-2}$, for example 6–700 kV. Such voltages require heavy shield configurations as shown in FIG. 1. It is therefore obvious that unilateral electron treatment at energies below full penetration capability might be expected to offer very non-uniform exterior-interior side wall and bottom treatment as well as inadequate interior neck treatment.

Preferred Process Geometry

Using 9 μm film dosimetry,[13] dose surveys over all surfaces of a container have been made using unilateral irradiation of the container along its longitudinal axis. This would typically utilize a scanned electron beam although a "curtain type" beam would be equally applicable[14]. This arrangement would typically involve the transport of the container through a beam whose transverse width is smaller than that of the container but whose longitudinal length is considerably longer than the container's height so that air scattered electrons bathe the exterior bottom and mouth opening in a relatively uniform manner. The geometry is shown in FIG. 3.

Figure 3:
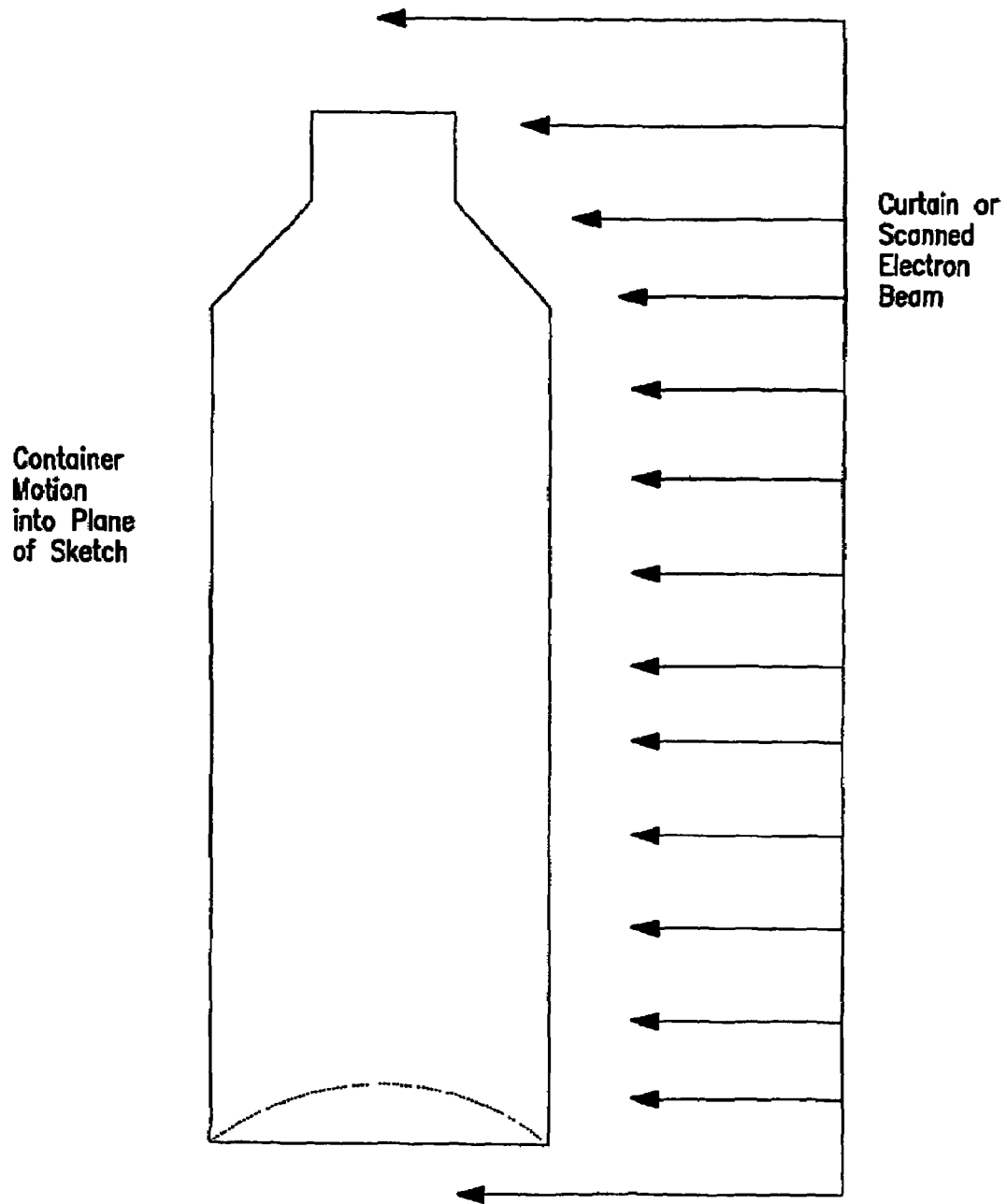
FIG. 3 is a diagram showing unilateral sterilization geometry for fluid containers.
Figure 4:
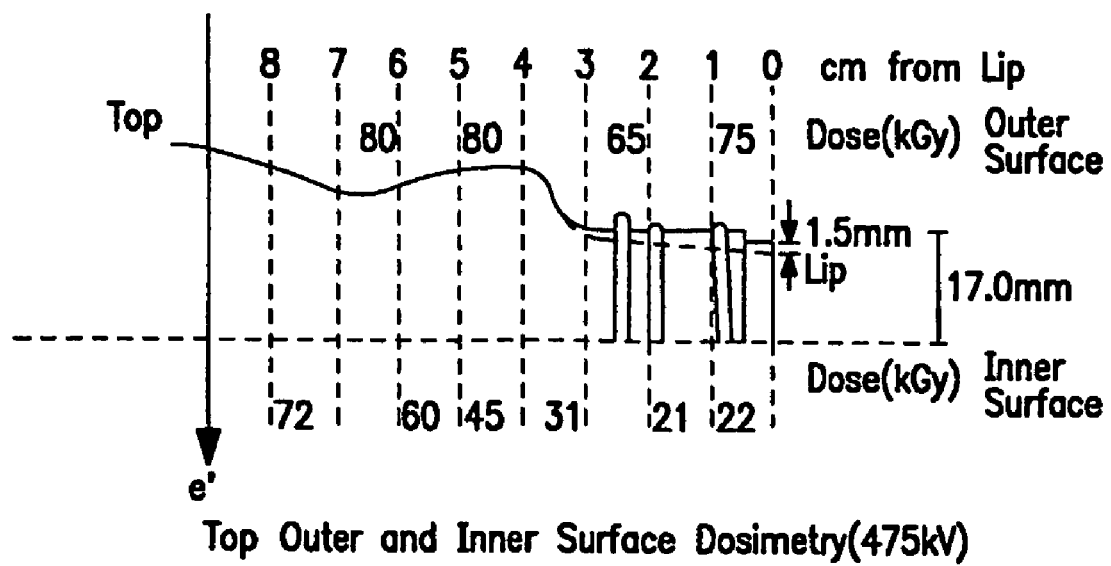
FIG. 4 is a diagram showing top outer and inner surface dosimetry at 475 kV.

The experimental dose distributions along the front (top) surface of the neck and its top interior are shown in FIG. 4 at a 475 kV operating voltage. As shown in FIG. 2, this operating point offers a half dose point of ~900 g.m$^{-2}$ and an end or maximum penetration of only 1400 g.m$^{-2}$, well below that required for neck or bottom penetration. However, the surface dose distributions for both regions under these operating conditions as shown in FIG. 4 are relatively uniform due to the scattering geometry offered by the container irradiation geometry illustrated in FIG. 3. For the 1-liter bottle shown, the uniformity was ±10% over the top exterior 6 cm from the mouth plane, and ±30% over the top interior 8 cm from the mouth plane.

Figure 5:
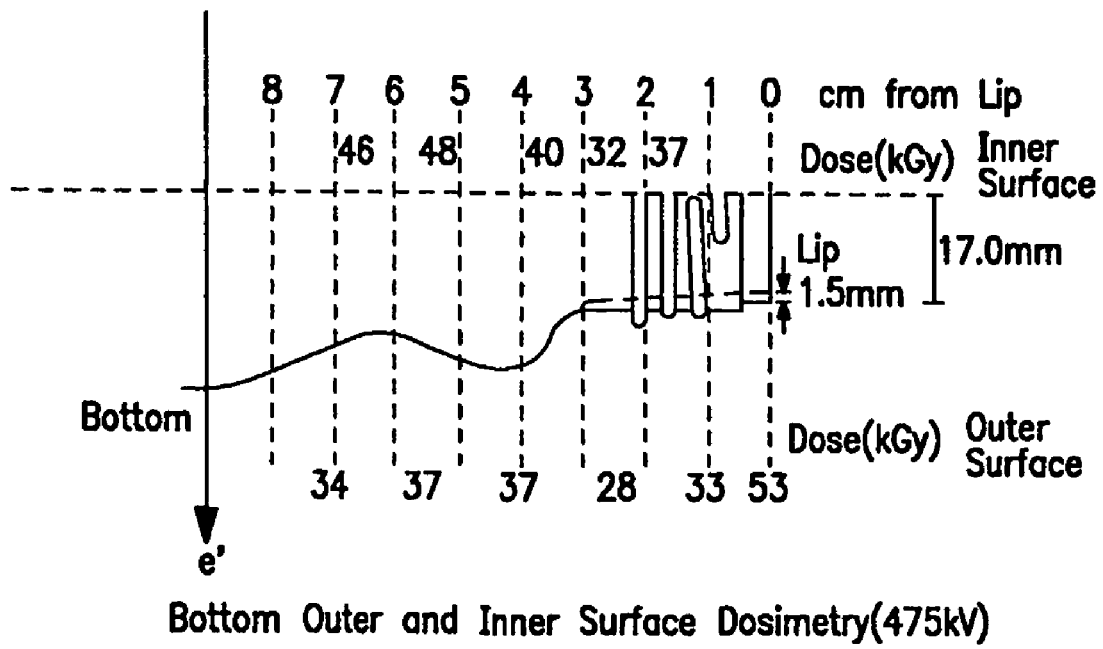
FIG. 5 is a diagram showing bottom outer and inner surface dosimetry at 475 kV.

Under these same conditions, the interior and exterior lower surface dose profiles are shown in FIG. 5. Here the interior lower surface demonstrated a uniformity of ±7% and an exterior rear (lower) surface uniformity of ±30% over 7 cm from the mouth plane. These results revealed the unexpected result that electrons incapable of full penetration of the thicker regions of the container could provide quite uniform treatment of the "protected" neck regions using the longitudinal treatment geometry.

Experimental studies conducted at 475 kV in a scanned machine with the preferred longitudinal orientation shown in FIG. 3, used 6 mm diameter support rails in order to simulate the "air conveyor" or pneumatic transport geometry. With the use of film dosimetry to map the rail contact interface on the outer surface of the container about its 360° periphery, it was found that with the 32 ounce container, the maximum/minimum dose ratio was reduced to under 2:1 with container rotation versus the 5:1 ratio measured with static, unilateral treatment.

Figure 6:
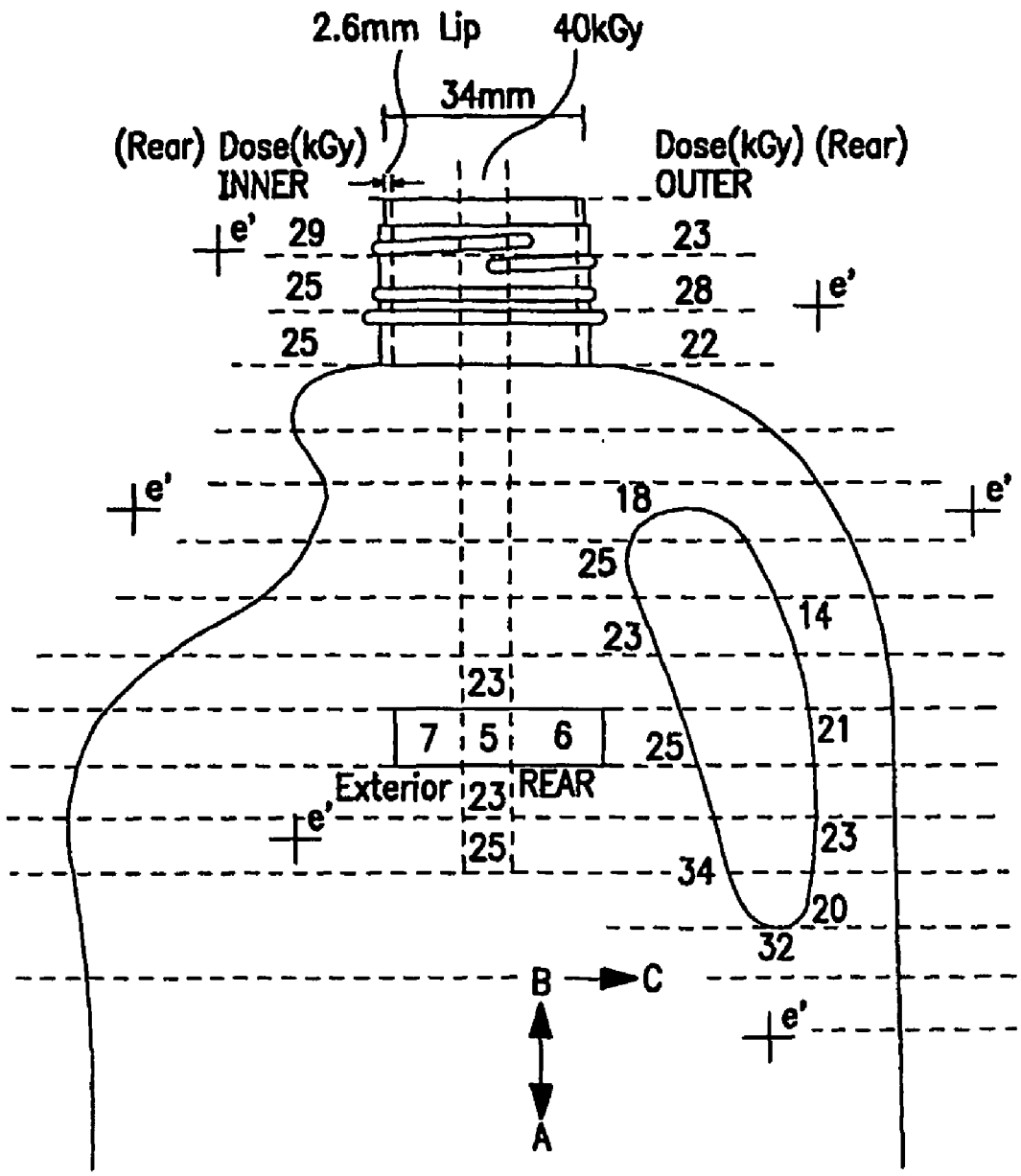
FIG. 6 is a diagram showing upper handle mouth region of 3-quart jug treated as in FIG. 3.
Figure 7A:
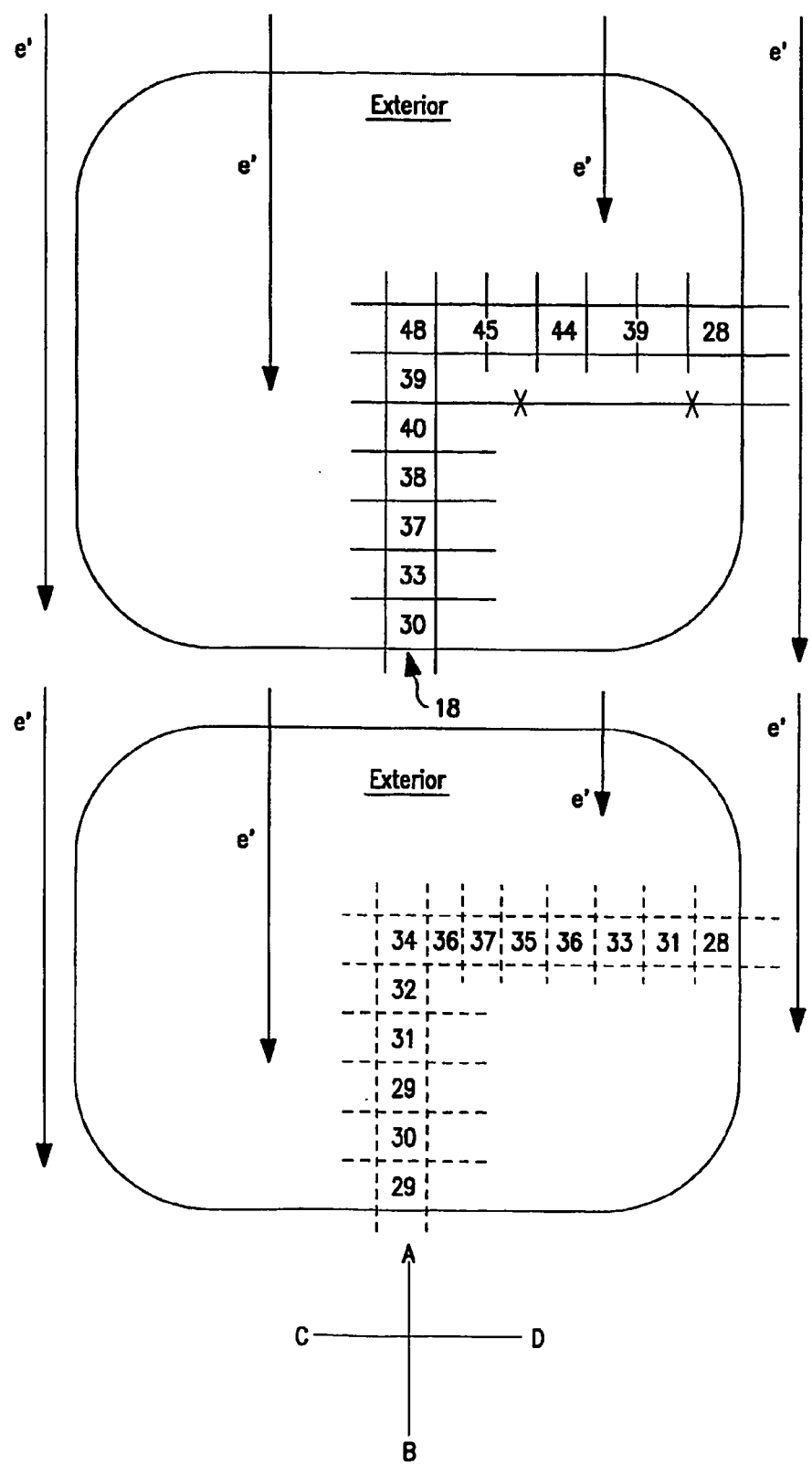
Figure 7B:
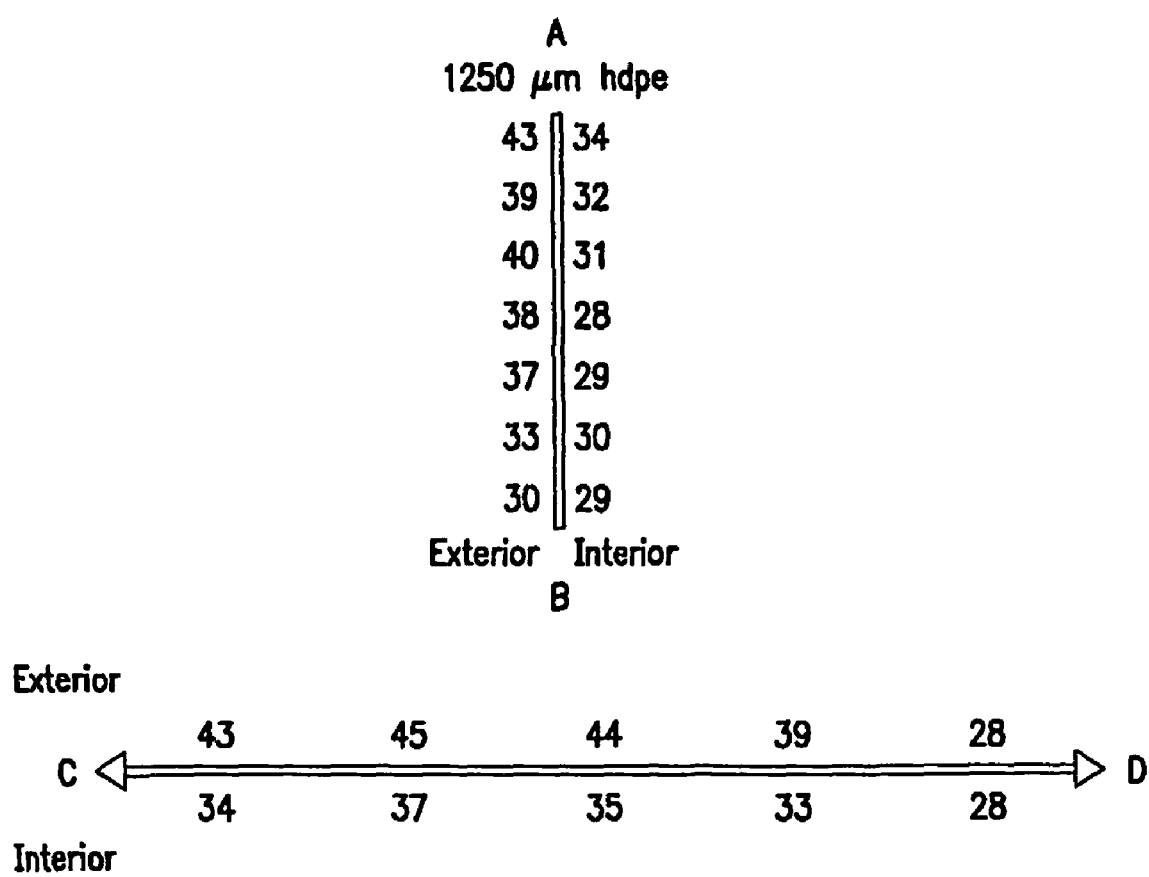

Similar results using the identical dosimetric film mapping technique are shown in FIGS. 6 and 7. FIG. 6 shows the dimensions of a 3 quart polyester jug with a hollow (normally liquid filled) handle whose walls are 1300 g.m$^{-2}$ thick and whose side wall range from 600–1200 g.m$^{-2}$. The electron beam longitudinal direction is shown by vectors AB, while the direction of transport of the container through the beam is shown by vector C of FIG. 6. The dose data shown for single pass treatment reveal a ±30% uniformity around the interior handle, and the same behavior of the dose distribution around the mouth opening as in the case of the 32 ounce bottle. The interior to exterior rear wall dose ratio was found to be 3:1, a figure much better than expected for the 1300–1400 g.m$^{-2}$ of material presented to the beam. The "side presentation" of the container to the beam was found to be necessary to improve the treatment uniformity at the handle plane.

FIG. 7 illustrates the bottom interior and exterior dose distributions. The exterior distribution shows excellent uniformity in both radial directions, while the interior shows similar uniformity (±10%). What is again unexpected is the good exterior to interior dose ratios of approximately unity. For the conditions employed in these trials at 550 kV operating voltage, the average treatment level throughout all surfaces of the jug was 25 kiloGrays. The lowest dose measured of 5 kGy was on the rear surface in the upper portion of the container. If one selects a minimum dose of 10 kGy for aseptic application, the overall dose would be doubled and an average surface dose (interior and exterior) of 50 kGy would result. Related extractables studies have shown this (upper) level to be quite acceptable for the widely used blow molded polymers, such as high density polyethylene and polyester, for bottle/jug manufacture.

For practicing the invention in commercial applications one would use a vacuum gripper which holds the bottle by its thin sidewall, so that the forward directed electrons can penetrate directly to the rear surface and deliver a sterilizing dose to that rear exterior surface immediately adjacent to the gripper.

Figure 8:
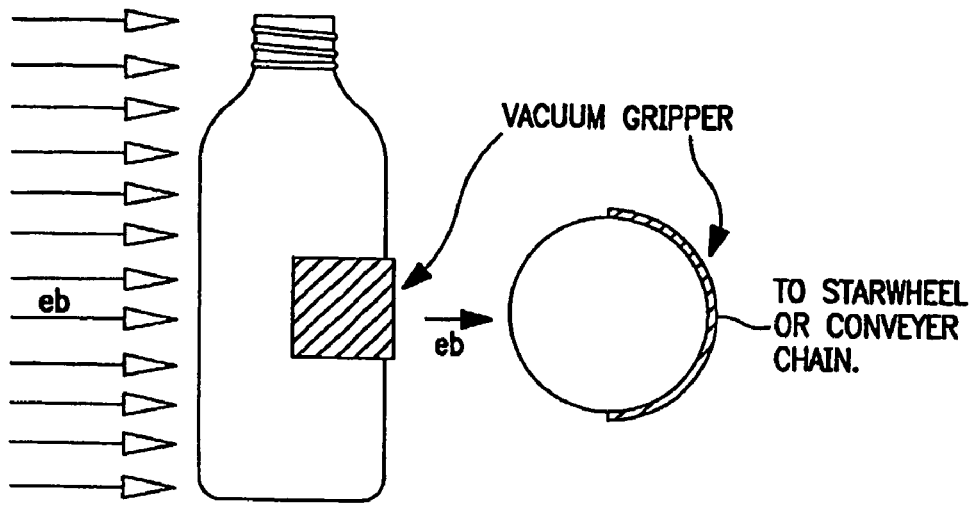
FIG. 8 is a diagram showing a vacuum bottle/jug gripper with ends free.

This arrangement is shown in FIG. 8 and holds the container in the treatment or sterilization zone so that both mouth opening and bottom surface are free and unblocked by any support or retainer mechanisms.

Figure 9:
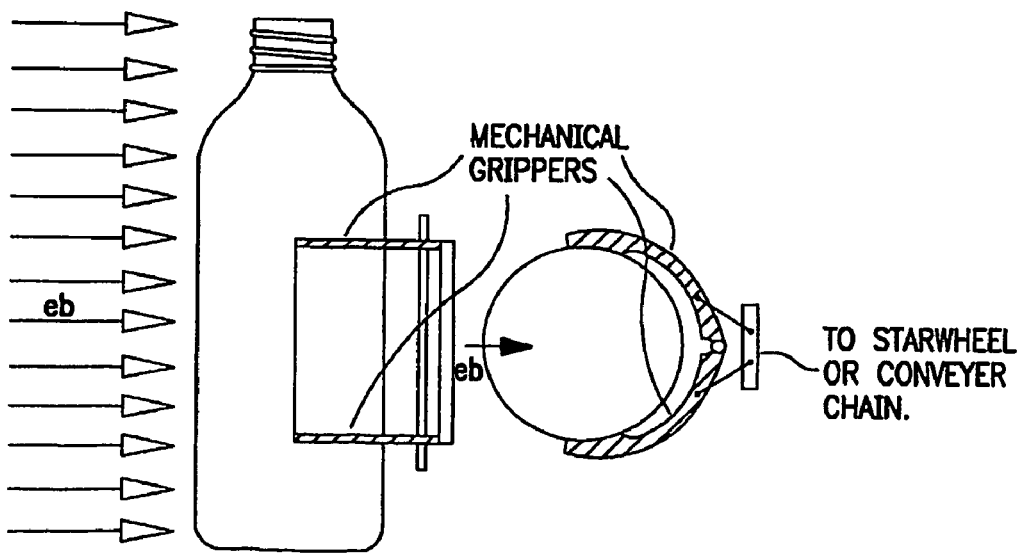
FIG. 9 is a diagram showing a spring-loaded gripper with ends free.

An alternate mechanical gripper is shown in FIG. 9, in which a 190-degree–200-degree spring-loaded gripper holds the bottle, again on its thinner central section where complete penetration of two wall thicknesses at the chosen sterilizer energy is feasible.

Figure 10:
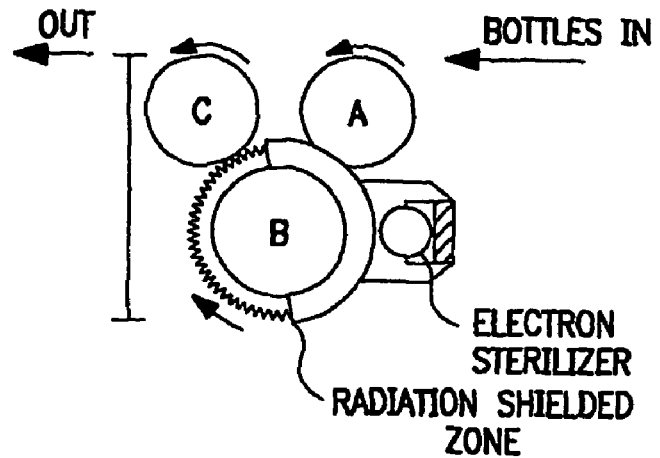
FIG. 10 is a diagram showing a general starwheel arrangement for electron sterilization.
Figure 11:
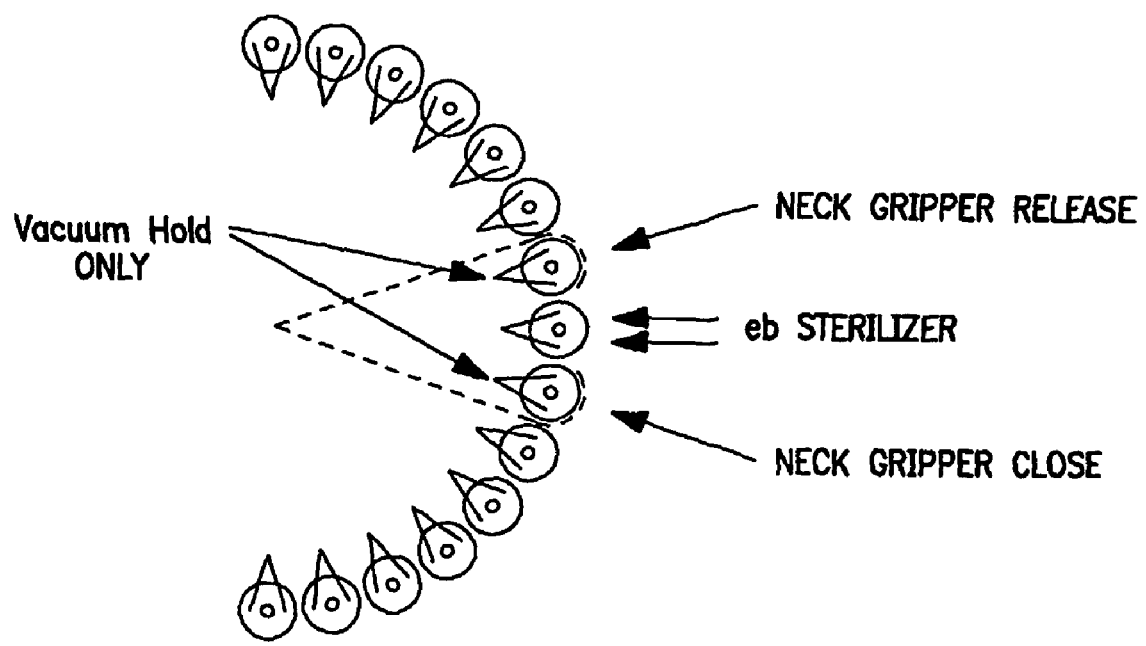
FIG. 11 is a diagram showing a neck gripper opened in sterilization zone only.

FIG. 10 shows the general arrangement for feeding the bottles using a conventional starwheel A to feed containers to the central wheel B. Pre-sterilization of the system is only required for wheels B and C (the take-off wheel) and the conveyor into the filler, usually a rotary type system which could be located on wheel C. Conventional gripping of the container (typically in the thicker walled neck region) is employed in A and C, while back-surface gripping described herein and shown in FIGS. 8 and 9 is used in wheel B to conduct the containers from A and to C (i.e. through the sterilization zone). The gripper sequence or spacing can be designed to accommodate containers of varying widths, so that, for example, wheels A through C can handle containers (e.g. 3 liter) of twice the width of the 1 liter container at half the throughput rate, with appropriate adjustment of the filler spout sequencing. Once again, after sterilization the container may immediately return to a conventional neck gripper for transfer off to starwheel C, so that, as shown in FIG. 11, the neck gripper need only be opened in the electron sterilization zone itself. Hence, starwheel B offers both gripping fixtures, only resorting to the rear-surface gripping in the eb treatment zone so that the containers are dependent on vacuum gripping alone over a small portion of their circular transport on B: i.e. less than or equal to 10 degrees. This mechanism allows the use of well-proved neck gripping techniques to be utilized in the electron sterilization process of the invention.

Figure 12:
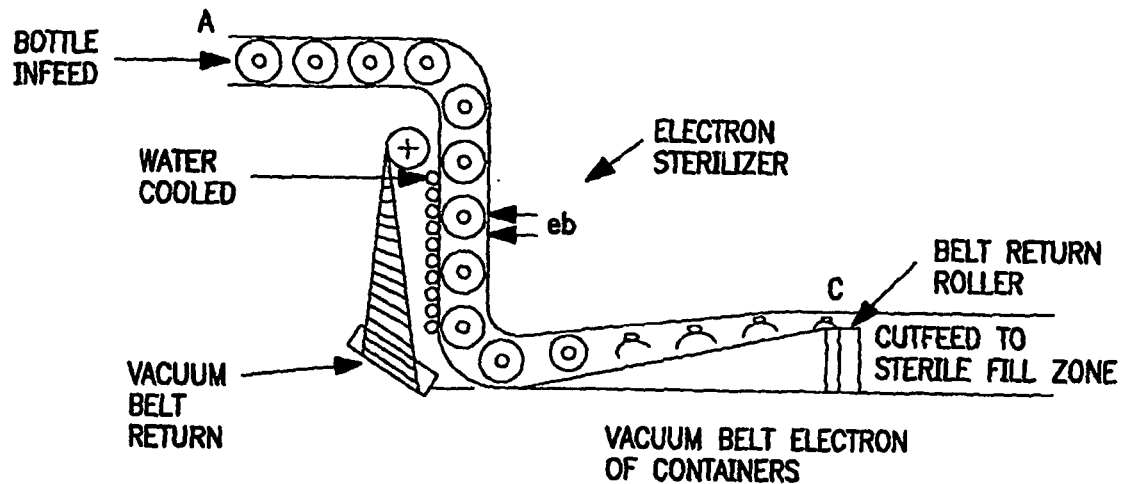
FIG. 12 is a diagram showing self-shielded bottle transport.

The invention includes unilateral electron beam treatment of the container as described hereinabove with a vertical container motion so that no contact is required with the container while in the treatment zone, thus providing electron access to all surfaces. Such vertical container motion is depicted in FIG. 12, in which the bottle drops ballistically or on a hold-down belt with no surface contact in a water-cooled duct into which the electron gun fires with an elongated and vertically oriented beam. Such a configuration may also be used with a horizontally oriented beam (as shown) of higher dose rate through which the container passes "ballistically" in its vertical drop from infeed A to outfeed C. The major difficulty with this attractive (shielding) geometry is the re-gripping of the container after sterilization, so that vacuum hold-down of the bottom of the vertically oriented, now-sterile container can be used for conveyor transport after sterilization. This transport system can be used for relocation by neck gripping on a filling/capping starwheel if desired, because the container is now in a fully sterilized state.

Figure 13:
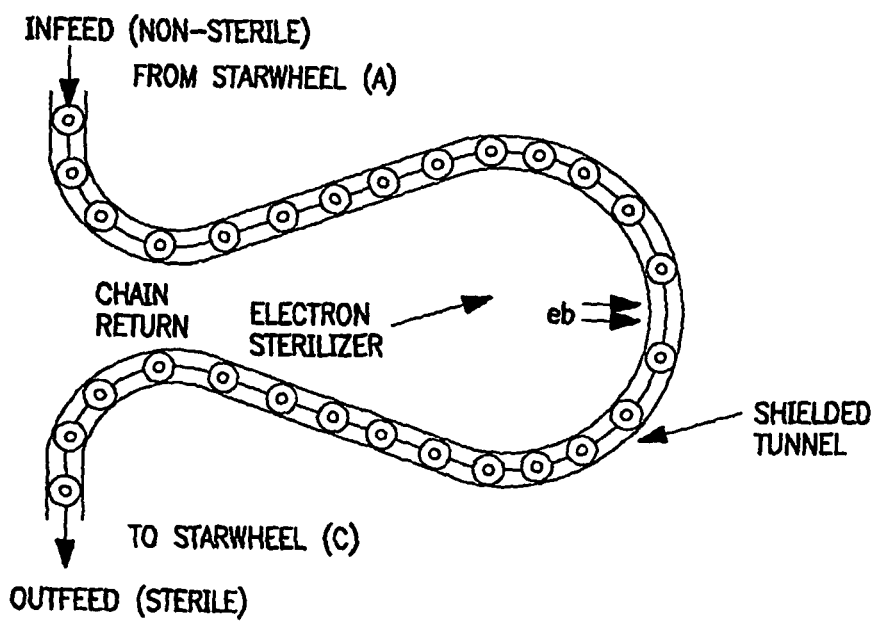
FIG. 13 is a diagram showing shielded tunnel geometry with mechanical grippers.

A more conventional but less compact shielded tunnel geometry with mechanical hold-down on the chain (FIG. 9) is shown in FIG. 13.

The process of the invention is most usefully applied in the sterilization of molded containers possessing a thick walled base, a thin walled central section, and a heavy walled neck and fill opening. This application includes both cylindrical (bottle) and rectangular (jug) geometries.

It is known that scattered electrons play an important role in energy deposition by either energetic electrons or gamma-rays. What is not obvious is the ability to sterilize all surfaces of a container in which large portions of its surface consist of wall thicknesses far beyond the range of the primary electrons. In essence, applicants have demonstrated the ability to choose a much reduced energy to effectively treat all surfaces due to the scattering processes described and dependent upon the ability of the primary beam to penetrate the intermediate sidewalls of the construction.

The teaching of the invention is made particularly valuable in the case of the requirement of a fully sterile container for the pre-sterilized filler-capper region, such as for large volume aseptic packaging of liquids. However, the invention also includes the vertical placement of the container with its exterior bottom "blocked". This will be acceptable in certain applications where sterile air flow about the fill opening is used to "isolate" the interior of the container from microorganism contamination on the lower exterior surface . . . for example in pharmaceutical filling.

In accordance with the invention, the multiply scattered secondary electrons are very important in the treatment of surfaces parallel to the direction of motion of the primary electron beam. In the present case, they play the same important role in illumination of both bottom surfaces, as well as uniform treatment of the interior and exterior surfaces of the thick walled neck and lip of the container.

The real issue with respect to the thickened portions is not blocking any portion of the exterior surface with grippers, support conveyors, etc., more because of the need for its unblocked exposure to direct and scattered electrons. As already discussed, the interior surfaces are bathed in air and container wall (polymer) scattered electrons, the prime sources of which are the primary electrons capable of penetrating the thin central sidewalls of the containers.

The invention includes the following features:
1. Unilateral electron beam treatment of all surfaces of a container with electron energies inadequate for full penetration of diametrically opposed walls. The energy range utilized for the process is for sterilizers operating in the 200–550 kV range.
2. Unilateral electron beam treatment of all surfaces with the longitudinal axis of the beam distribution oriented along the container's longitudinal axis of symmetry.
3. Unilateral electron beam treatment of the container oriented in such a manner so as to prevent interior shielding of the food contact surfaces by the molded handle or by sections of the container walls which may be totally absorbing to the primary beam.

4. Unilateral electron beam treatment of the container in the manner described in 1 and 2, providing uniform treatment of the interior bottom from electrons penetrating the side wall and of the exterior bottom by air scatter from the primary beam.

5. Unilateral electron beam treatment of the container in the manner described in 1 and 2 with a vertical container motion so that no contact is required with the container while in the treatment zone, thus providing electron access to all surfaces.

6. Unilateral electron beam treatment of the container in the manner described in 1 and 2 with rotational motion of a vertical container about its longitudinal symmetry axis so that regions of rail support affecting electron access to the container surface are sufficiently treated.

7. Unilateral electron beam treatment of the container in the manner described in 1 and 2 with fixed mechanical gripping or vacuum hold-down of the container with good definition and control of the sterile zone around the fill opening, so that any microorganisms from these non-sterile exterior areas cannot reach the interior surfaces during the filling and capping process.

8. Physical organization of container handling machinery so that the electron beam treatment zone defines the region before which pre-sterilization is not necessary and beyond which pre-sterilization and sterile operational maintenance are required.

REFERENCES

1. Nablo, S. V., Cleghorn, D. A. and Fletcher, P. M., "Dose Distributions for Containers Electron Sterilized at Energies from 150–250 keV.", Rad. Phys. Chem. 42, # 4–6, 827–831 (1993).
2. Nablo, S. V., "Process and Apparatus for Surface Sterilization of Materials", U.S. Pat. No. 3,780,308, Dec. 18, 1973; Nablo, S. V. and Cleghorn, D. A., "Technique for Interior Electron Sterilization of an Open Mouthed Container", U.S. Pat. No. 6,221,216, Apr. 24, 2001.
3. Auslender, V. L. et al, "Automated Technological Radiation Installation for Sterilization of Medical Goods", Rad. Phys. Chem. 52, 459–465, (1998).
4. Inai, T., Akai, T., Iwano, F., Yamamato, E. and Ueda, M., "Sterilization Treatment for Tubular Packaging Material", Japanese Patent Hei 11-35015, November (1999).
5. Mittendorfer, J., Bierbaumer, H. P., Gratxl, F. and Kellauer, E., "Decontamination of food packaging using electron beam—status and prospects," Radiation Physics and Chemistry 63, 833 (2002).
6. Private communication, Sentry Equipment Inc., 13150 East Lynchburg Salem Tpke. Forest, Va. 24551.
7. 29 CFR 1910. 1096, "Ionizing Radiation", USGPO Washington (1996).
8. "Safety Standard for Non-Medical X-Ray and Sealed Gamma-Ray Sources", Handbook 93, US Dept. of Commerce, Washington, D.C. (1963).
9. Cleghorn, D. A., Dunn, J. and Nablo, S. V., "Sterilization of Plastic Containers Using Electron Beam Irradiation Directed Through the Opening", Journal of Applied Microbiology 93, 937–943 (2002). See also Proc. World-Pak 2002, Vol 1, 81–90, MSU School of Packaging, June 23–28, CRC Press New York (2002).
10. Sadat, T. and Huber, T., "E Beam—a new transfer system for isolator technology," Radiation Physics and Chemistry 63, 587 (2002).
11. "Charged Particle Range" section 3.6.3, *Radiation Shielding* ed. J. K. Shultis and R. E. Faw, Prentice Hall PTR, N.J. (1996).
12. "Practice for Dosimetry in an Electron Beam Facility for Radiation Processing at Energies between 80 and 300 keV.", ASTM Standard E 1818–96, 2000 Annual Book of ASTM Standards, ASTM, 100 Barr Harbor Drive, PO Box C700, West Conshohocken, Pa. 19428-2959.
13. FWT Radiachromic Film Type 60-810, Far West Technology Inc., 330-D South Kellogg Avenue, Goleta, Calif. 93117.
14. Unscanned electron processors of this type are manufactured and sold under the trade names Electrocurtain® and EZ Cure® by Energy Sciences Inc., 42 Industrial Way, Wilmington, Mass. 01867.

Having thus described the principles of the invention, together with several illustrative embodiments thereof, it is to be understood that, although specific terms are employed, they are used in a generic and descriptive sense, and not for purposes of limitation, the scope of the invention being set forth in the following claims:

The invention claimed is:

1. That method of irradiating, in a gaseous medium, a hollow open-mouthed container having an axis and having walls of varying thickness, which method comprises
   directing primary electrons laterally against said container as a sheet extending along said axis and more than the length of said axis,
   said primary electrons having energy insufficient to penetrate through the entire container (i.e. two walls) at the thicker portions of said walls but sufficient to penetrate the entire container (i.e. two walls) at the thinner portions of said walls,
   the dose delivered to said thicker portions by said primary electrons being supplemented by secondary electrons produced by scattering of said primary electrons by said gaseous medium and said container.

2. Method of using reduced electron energy for the sterilization of preformed open-mouthed containers, comprising the following steps:
   producing an electron sheet in an electron-scattering gaseous region with a cross-sectional length L and width W,
   conveying an open-mouthed container having an axis with a length less than L transversely through said sheet in such a manner that the extremities of said sheet by-pass said container while the region between said extremities passes through said container,
   said axis being parallel to said sheet as said container passes through said sheet,
   the energy of said electrons being sufficient to provide the required minimum dose to all surfaces of said container while remaining below that required for full penetration of the thicker regions of the container.

3. Method in accordance with claim 2, wherein the maximum treatment level delivered by said electrons remains below the threshold dose at which said electrons cause damage to said container.

* * * * *